(12) United States Patent
Parrill-Baker et al.

(10) Patent No.: US 8,343,934 B2
(45) Date of Patent: Jan. 1, 2013

(54) DIVERSE LEAD COMPOUND AUTOTAXIN INHIBITORS

(75) Inventors: Abby Louise Parrill-Baker, Memphis, TN (US); Daniel Lee Baker, Memphis, TN (US); Elton Jeffrey North, Memphis, TN (US)

(73) Assignee: University of Memphis, Memphis, TN (US)

( * ) Notice: Subject to any disclaimer, the term of this patent is extended or adjusted under 35 U.S.C. 154(b) by 300 days.

(21) Appl. No.: 12/828,053

(22) Filed: Jun. 30, 2010

(65) Prior Publication Data

US 2011/0160148 A1    Jun. 30, 2011

Related U.S. Application Data

(60) Provisional application No. 61/222,022, filed on Jun. 30, 2009.

(51) Int. Cl.
*A61K 31/655* (2006.01)
*C07C 309/52* (2006.01)
*C07C 245/10* (2006.01)

(52) U.S. Cl. ........ 514/21.9; 514/150; 514/576; 514/577

(58) Field of Classification Search .......... 514/21.9, 514/150, 576, 577
See application file for complete search history.

(56) References Cited

U.S. PATENT DOCUMENTS 4,959,383 A * 9/1990 Hall .............................. 514/381

* cited by examiner

*Primary Examiner* — Raymond Henley, III
(74) *Attorney, Agent, or Firm* — Wyatt, Tarrant & Combs, LLP; William S. Parks

(57) ABSTRACT

Classes of compounds that exhibit effective inhibition of autotaxin enzymes are provided. Such classes include naphthalenesulfones, phenylsulfones, and certain peptides with unnatural amino acids and exhibit reactivity with autotaxin to ultimately reduce the size of the reactive sites thereon to prevent conversion of lysophosphatidyl choline to lysophophatidic acid. Furthermore, such compounds can be incorporated within delivery forms for human ingestion. As such, these compounds accord an excellent manner of potentially reducing generation of certain cancers attributable to the presence of naturally occurring autotaxin within the human body. Methods of inactivating autotaxin to certain degrees therewith such compounds are encompassed within invention as well.

14 Claims, 1 Drawing Sheet

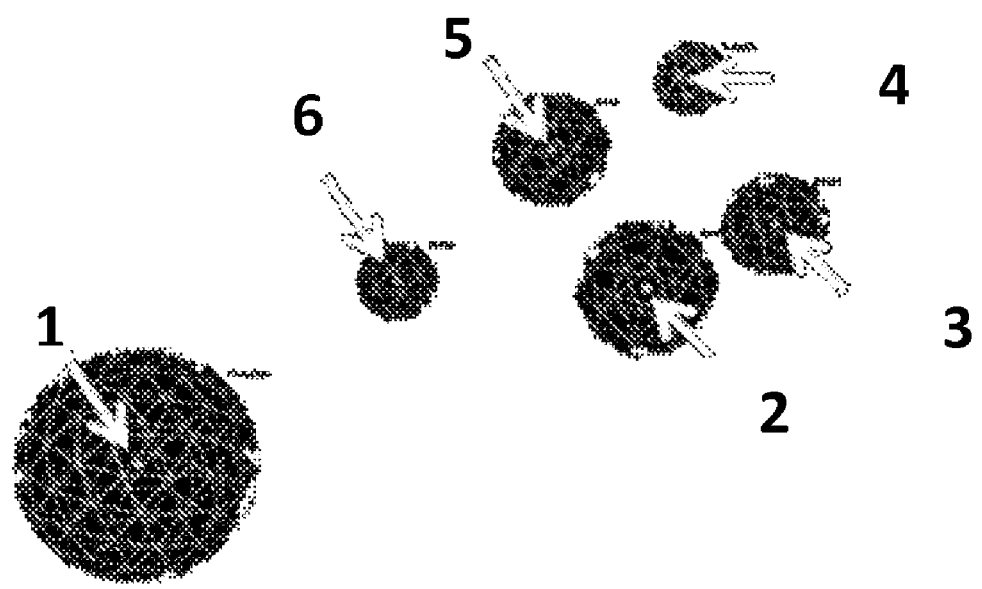

DIVERSE LEAD COMPOUND AUTOTAXIN INHIBITORS

CROSS-REFERENCE TO RELATED APPLICATION

This application claims priority to Provisional Application 61/222,022, filed on Jun. 30, 2009, the content of which is incorporated entirely herein by reference.

FIELD OF THE INVENTION

Classes of compounds that exhibit effective inhibition of autotaxin enzymes are provided. Such classes include naphthalenesulfones, phenylsulfones, and certain peptides with unnatural amino acids and exhibit reactivity with autotaxin to ultimately reduce the size of the reactive sites thereon to prevent conversion of lysophosphatidyl choline to lysophophatidic acid. Furthermore, such compounds can be incorporated within delivery forms for human ingestion. As such, these compounds accord an excellent manner of potentially reducing generation of certain cancers attributable to the presence of naturally occurring autotaxin within the human body. Methods of inactivating autotaxin to certain degrees therewith such compounds are encompassed within invention as well.

BACKGROUND OF THE PRIOR ART

All U.S. patents cited within this specification are hereby incorporated by reference.

Autotaxin, also known as ATX, ENPP2 or NPP2, short for Ectonucleotide pyrophosphatase phosphodiesterase 2 is an enzyme secreted within the human body. This molecule has been known for generating (LPA) through conversion of lysophosphatidyl-choline (LPC) thereto via lysophospholipase D activity (the removal of choline from the base compound generates LPA). LPA has been realized to contribute to tumor cell growth, unfortunately, as the reactivity within the human body of LPA within certain tissues has resulted, in certain studies, in cancerous growths when present at certain levels. In this manner, then, it has been theorized that the greater the incidence of autotaxin activity within the human body, the greater the possibility of LPA generation. A reduction in the catalytic capabilities of autotaxin to convert the LPC molecule to LPA would theoretically permit an ultimate reduction in possibility of unwanted cell proliferation through reduced LPA presence within a subject's body.

The mechanism of autotaxin in terms of enzymatic activity and catalysis to form LPA resides in its phosphodiesterase capability. LPA can be generated from the cleavage of the phosphodiester bonds of LPC, through the function of a phospholipase enzyme (note Formula I).

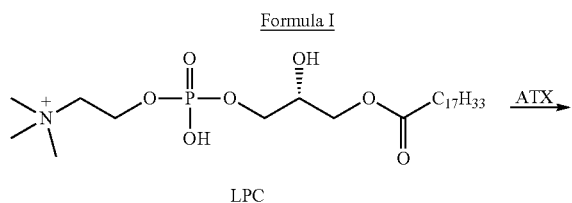

LPC

Formula I

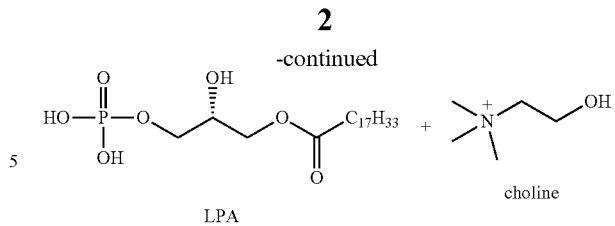

LPA choline

In extracellular fluids, this enzymatic catalysis of LPC removes the choline group, leaving LPA, which has a tendency to stimulate cell growth and proliferation as well as chemotaxis. From this, it appears that the motility of tumor cells is increased as well, resulting in properties and gene expression within certain carcinomas (such as, for instance, breast cancer cells), causing further processing into a form that is bioactive and potentially dangerous. Metastasis and oncogenesis of cancer cells appear to occur as well with elevated levels of LPA present within a targeted region. Increased ATX expression has been identified in renal carcinoma, metastatic breast cancer, thyroid carcinoma, Hodgkin lymphoma, and invasive glioblastoma multiforme.

It has thus been determined that the ability to prevent, or at least reduce, the amount of LPA within the human body holds great promise at, likewise, reducing, if not preventing, the onset of certain cancers. It has been theorized, as noted above, that autotaxin modifications may prevent the undesirable conversion from LPC to LPA; the ability to actually accomplish such a result has been elusive, however, at least to the degree necessary for effective broad-scale utilization of such a method. Any modification thereof must exhibit an ability to drastically reduce the activity of autotaxin while also, preferably exhibiting oral bioavailability as well.

Past work at ATX inhibition has included L-histidine. Unfortunately, millimolar concentrations were required for any efficacy, and, more importantly, zinc sulfate reversal of this effect (in submillimolar concentrations) suggested an inhibition mechanism involving interaction with the two native active site metal ions thereof. Other potential ATX inhibitors have included the products of ATX-catalyzed hydrolysis of LPC and sphingosyl phosphorylcholine (SPC), LPA, and S1P, respectively. Inhibition of ATX by LPA and S1P suggests that product feedback inhibition may contribute to regulation of ATX function in vivo. Additional reported ATX inhibitors share several common structural features, including a phosphate, thiophosphate, or phosphonate headgroup attached either with or without a linker to an alkyl chain, which can vary in overall length and can be either saturated or unsaturated. However, these compounds both lack substantial structural diversity and fail to meet Lipinski's empirical rules that characterize 90% of orally bioavailable drugs. It is of great importance to identify novel non-lipid structural classes capable of inhibiting ATX and which are orally bioavailable to treat certain tumor classes. ATX inhibitors consistent with Lipinski's rules have been identified using model-based structural screening, such as within U.S. Provisional Patent Application 61/002,687, entitled "Method for the Identification of Compounds Used in the Treatment of Certain Tumors Using Autotaxin Inhibitors as Chemotherapeutic Compounds and the Method of Treating Tumors Using Those Compounds," filed on Nov. 13, 2007, and by large-scale screening of libraries of phosphodiesterase and kinase inhibitors.

It is believed, without relying upon any specific scientific basis, that the lack of diversity in reported ATX inhibitors, as noted above, is due, in part, to the lack of a characterized three-dimensional structure of the enzyme. The ATX sequence of over 860 amino acids is divided into several domains, including a central catalytic domain composed of about 400 amino acids. ATX is a member of the nucleotide pyrophosphatase/phosphodiesterase (NPP) family, as well as the alkaline phosphatase superfamily. Crystallographic structures of several alkaline phosphatase superfamily members have been available for decades. These crystal structures show remarkable structural conservation in a small core surrounding the catalytic site, but unfortunately show completely different structural characteristics outside this conserved core. Sequence homology of the alkaline phosphatases with ATX does not exceed 14% and is therefore insufficient for generation of a high quality homology model in any region outside the approximately 100 amino acid structurally conserved core. The recent report of a crystal structure of a bacterial NPP enzyme with 30% identity to the ATX catalytic core domain enabled the development of a structural model of the ATX catalytic domain that may prove useful in structure-based drug design. Although a significant improvement, such a homology model must be applied cautiously as involvement of the c-terminal nuclease-like domain in substrate recognition has been suggested from studies of NPP family domain-swapping chimeras. In any event, these previously reported ATX inhibitors are analogs of LPA, a phospholipid, and are more hydrophobic than is typical of orally bioavailable drugs, thereby creating problems in that area.

As such, there exists a definitive lack in providing effective ATX inhibition (or inactivation) within the current knowledge base in this area, particularly as it concerns compounds that not only exhibit ATX inhibition, but also meet certain oral bioavailability requirements (as measured by Lipinski's rules). As noted above, previous attempts at such treatments have provided developments of certain classes of compounds that exhibit certain desired results with ATX inhibition. However, the generation of classes that effectively provide increased overall ATX inhibition characteristics has been lacking in the pharmaceutical industry.

ADVANTAGES AND BRIEF DESCRIPTION OF THE INVENTION

It is thus an advantage of the present invention to provide reliable autotaxin inactivators for the purpose of reducing the conversion of LPC to LPA through the utilization of a readily available and easily produced compound (or compounds) that does not pose any significant health risks and exhibit the necessary oral bioavailability requirements. Another advantage is the ability for treatment with such compounds for cancer prevention treatment regimens. yet another advantage is the potential capability of providing combinations of different compounds that are similar in foundational structure that may exhibit a synergistic effect for further improved ATX inhibition.

Accordingly, this invention encompasses a method for treating a patient to reduce autotaxin activity within the subject patient's body, said method involving the introduction within the subject patient of at least one compound selected from the group consisting of at least one naphthalene sulfone, at least one phenylsulfone, at least one peptide including unnatural amino acids, and any mixtures thereof.

This inventive method thus concerns the treatment, via any available manner, such as intravenous, oral ingestion, and the like, of a mammalian subject to reduce autotaxin availability therein. Such an inventive method may also encompass the broad treatment of the same subject for a number of different maladies associated with autotaxin presence and activity within the subject's body (such as to treat obesity, atherosclerosis, and the like, as noted herein), rather than simply for cancer treatments alone.

The inventive compounds for such a method have been developed in relation to the ATX inhibition capability predicted through a modified pharmacophore modeling process. In essence, these compounds were derived through the initial utilization of known structures to develop a pharmacophore from which further comparisons may be made. Such a ligand-based pharmacophore includes six distinct base point functions that appear to be present within each of the previously known structures, in terms of group size and distance between functions, that would react in a proper fashion with the ATX molecule (of large size, as noted above) to deactivate such an enzyme from converting LPC to LPA. Generally, eight previously identified non-lipid ATX inhibitors were built using MOE and ionized as predicted at biological pH to emulate internal metabolization possibilities. Such compounds were then flexibly aligned onto one another to identify the aforementioned functional groups that share common volumes. The six identified pharmacophore base points were, as follows: an anionic group (point 1), two hydrogen bond acceptors/metal ligators (points 2 and 4), two aromatic groups (points 3 and 5), and one hydrogen bond donor (point 6). In terms of initial comparisons with known compound databases, this six-point approach proved too restrictive; no hits were found for further testing. Thus, it was reasoned that a pared-down approach was necessary to generate any suitable hits at all. In this manner, it was decided to remove one of the aromatic points as well as one of the hydrogen bond/metal ligator points (points 2, 3, 4, or 5), to reduce the number of points necessary for database comparisons. Additionally, however, it was hypothesized that removal of consideration of any of these points was suitable due to the expected chelation most likely prevalent with divalent metals in the active site. The resultant four 5-point pharmacophores were generated with each lacking one of points 2, 3, 4, and 5; additionally, four 4-point pharmacophores were generated each lacking one aromatic and one hydrogen bond acceptor/metal ligator. From this basis, a suitable number of nine pharmacophores were each used to search the National Cancer Institute (NCI) Database for any compounds present therein. From there, a list of 254 compounds was generated, of which only 126 were available for biological utilization due to the presence of an anionic group for ionization at a proper pH. From this list, 102 of those compounds were available for further autotaxin inhibition/inactivation testing. The final determination was that 27% of those 102 compounds would exhibit suitable ATX inhibition/inactivation capability as well as proper biological and oral ingestable characteristics, thus leading to the potential development of a relatively large number of suitable ATX inhibiting compounds through a small modicum of actual time and resources, a noticeable and significantly more efficient improvement over prior research and development practices.

It is preferable that such compositions be orally ingestable, but they may, as noted above, be provided for intravenous introduction as well.

In terms of the form such compositions may take, any orally ingestable form is possible. This list includes, without limitation, liquids, liquid capsules, tablets, coated tablets, minitablets, capsules with individual beads, and the like. If in coated tablet form, such compositions may be of sustained release type, and may include a water insoluble but permeable film coating surrounding a core tablet and a particulate, water-soluble, pore-forming material dispersed within the film coating. Such a system thus provides an osmotic gradient and channel forming system. Typical coatings have included carnauba wax, cysteine hydrochloride, hydroxypropyl methylcellulose, magnesium stearate, microcrystalline cellulose, polyethylene glycol and titanium dioxide. Other therapeutic agents may be included with these anticancer (autotaxin inhibiting) agents as well, as long as neither interferes with the effectiveness of the other in the user's body.

BRIEF DESCRIPTION OF THE DRAWING

The FIGURE shows an inventive pharmacophore characterized by an anionic function (1), two hydrogen bond acceptors/metal ligator functions (points 2 and 4), two aromatic group functions (points 3 and 5), and one hydrogen bond donor function (point 6).

DETAILED DESCRIPTION OF THE DRAWING AND INVENTION AND PREFERRED EMBODIMENTS

The specific compounds below, as well as the following exemplified methods of producing using such compounds are non-limiting in nature and are thus indicative of the preferred embodiments of this invention.

As noted above, this invention is directed to a novel method of treating patients with suitable ATX inhibiting compounds. Such compounds were determined through a very efficient screening procedure, and exist as lead compounds with the potential to treat metastasis, obesity, neuropathic pain, atherosclerosis and rheumatoid arthritis, at least, within a mammalian body. As described above, the autotaxin (ATX) enzyme promotes cell migration and invasion, thus inhibition of ATX is of value for prevention of metastasis and the other maladies noted previously.

In terms of the screening procedure, initially the process involved the generation of a proper pharmacophore based upon the structures of already known effective autotaxin inhibiting compounds. FIG. 1 provides the parent six-point pharmacophore generated based upon comparison with previously known, acceptable ATX inhibitors. Specifically, a large anionic group function must be present for proper ionization at a biological pH level; the metal ligators present (as noted above) coupled with the aromatic groups and the hydrogen bond donor, all contribute in some fashion to the reactivity necessary with the large ATX enzyme. As discussed previously, however, this parent pharmacophore proved too restrictive to determine any discernible comparisons with compound databases; no proper hits were found, in essence. This led to the unexpectedly surprising result that removing one or two of the 2, 3, 4, or 5 functions from the parent pharmacophore accorded a 5 or 4-point pharmacophore that permitted further comparisons. With a limited number of comparative base point functions, generation of suitable results in terms of effective ATX inhibiting compounds was not expected. However, in order to further determine suitable compounds, it was decided to narrow the possibilities of the remaining base point function comparisons, in terms of volumes and distances therebetween, in essence, to certain ranges of possibilities. Table 1, below, shows all the distances measured and among the pharmacophore points and the distance ranges chosen to then make a proper search of a comparison database for available compounds (such as the NCI database).

TABLE 1

Pharmacophore point distances and ranges used to search the NCI database.

| Points | Distance (Å) | Range Searched (Å) |
|---|---|---|
| Pharmacophore 4a (Points 1, 2, 3, and 6) | | |
| 1-2 | 11.96 | 11-13 |
| 1-3 | 15.04 | 14-16 |
| 1-6 | 8.86 | 8-10 |
| 2-3 | 3.77 | 2.75-4.75 |
| 2-6 | 5.68 | 4.5-6.5 |
| 3-6 | 9.25 | 8.25-10.25 |
| Pharmacophore 4b (Points 1, 2, 5, and 6) | | |
| 1-2 | 11.96 | 10-14 |
| 2-5 | 3.66 | 2-5 |
| 5-6 | 4.32 | 3-5 |
| 1-5 | 11.82 | 10-14 |
| 1-6 | 8.86 | 7-11 |
| 2-6 | 5.68 | 4-7 |
| Pharmacophore 4c (Points 1, 3, 4, and 6) | | |
| 1-6 | 8.86 | 7.5-10 |
| 3-4 | 3.97 | 3-5 |
| 3-6 | 9.25 | 8-10.5 |
| 1-3 | 15.04 | 14-16 |
| 1-4 | 14.82 | 13.5-15.5 |
| 4-6 | 7.93 | 7-9 |
| Pharmacophore 4d (Points 1, 4, 5, and 6) | | |
| 1-4 | 14.82 | 14-16 |
| 1-5 | 11.82 | 11-13 |
| 1-6 | 8.86 | 8-10 |
| 4-5 | 3.66 | 2.5-4.5 |
| 4-6 | 7.93 | 7-9 |
| 5-6 | 4.32 | 3-5 |
| Pharmacophore 5a (Points 1, 3, 4, 5, and 6) | | |
| 1-6 | 8.86 | 7.5-10 |
| 3-5 | 5.97 | 5-7 |
| 3-6 | 9.25 | 8-10.5 |
| 1-3 | 15.04 | 14-16 |
| 1-4 | 14.82 | 13.5-15.5 |
| 4-6 | 7.93 | 7-9 |
| Pharmacophore 5b (1, 2, 4, 5, and 6) | | |
| 1-2 | 11.96 | 11-13 |
| 2-4 | 4.58 | 5.5-6.5 |
| 2-6 | 5.68 | 4.5-6.5 |
| 2-5 | 3.66 | 2.5-5 |
| 1-4 | 14.82 | 13.5-15.5 |
| 4-6 | 7.93 | 7-9 |
| Pharmacophore 5c (Points 1, 2, 3, 5, and 6) | | |
| 1-2 | 11.96 | 10-14 |
| 2-3 | 3.77 | 2.5-5.5 |
| 3-5 | 5.97 | 4-8 |
| 2-6 | 5.68 | 4-7 |
| 1-5 | 11.82 | 10-14 |
| 5-6 | 4.32 | 3-6 |
| Pharmacophore 5d (Points 1, 2, 3, 4, and 6) | | |
| 1-2 | 11.96 | 11-13 |
| 2-4 | 4.58 | 5.5-6.5 |
| 3-6 | 9.25 | 8-10.5 |
| 1-3 | 15.04 | 14-16 |
| 1-4 | 14.82 | 13.5-15.5 |
| 4-6 | 7.93 | 7-9 |
| Pharmacophore 6 (Points 1, 2, 3, 4, 5, and 6) | | |
| 1-6 | 8.86 | 7.5-10 |
| 3-5 | 5.97 | 5-7 |
| 3-6 | 9.25 | 8-10.5 |
| 1-3 | 15.04 | 14-16 |
| 1-4 | 14.82 | 13.5-15.5 |
| 4-6 | 7.93 | 7-9 |

From these results, the number of comparative hits meeting these critical measurements were located within the NCI database. After acquiring the compounds that were identified from the pharmacophore searches, a comparison was made in order to identify all the unique structures from the virtual screen. Table 2 shows the comparative results then of the compounds located from such a comparison.

TABLE 2

Hit acquirement and refinement.

| Pharmacophore | Number of Hits | Total Unique Hits | Unique Ionizable Hits | Acquired Hits |
|---|---|---|---|---|
| 4a | 13 | 160 | 126 | 102 |
| 4b | 31 | | | |
| 4c | 71 | | | |
| 4d | 71 | | | |
| 5a | 8 | | | |
| 5b | 35 | | | |
| 5c | 3 | | | |
| 5d | 21 | | | |
| 6 | 1 | | | |

Of 254 total structures identified from the pharmacophore searches, 160 were unique. From those 160 compounds, 126 actually would ionize at biological pH, since pharmacophore point 1 is an anionic functional group. As noted above, 102 out of the remaining 126 compounds ere then tested. These compounds were then analyzed for ATX inhibition capability, as described below.

ATX Inhibition Assay

ATX inhibition was assayed using the substrate FS-3 (Echelon Biosciences, Inc., Salt Lake City, Utah, USA). The FS-3 assay used ~10 times concentrated conditioned serum-free medium (CCM) from MDA-MB-435 cells as the source of ATX, while CCM comprised one-third of the total volume. The final volume for FS-3 was comprised of the substrate at varying concentrations and 30 µM charcoal-stripped fatty acid free BSA (Sigma Aldrich) in assay buffer (1 mM each $CaCl_2$ and $MgCl_2$, 5 mM KCl, 140 mM NaCl, 50 mM Tris pH 8.0).

All assays were performed in 96-well plates with data read at 1 minute intervals by a Synergy2 system (BioTek, Winooski, Vt.). The fluorescence produced upon the hydrolysis of FS-3 was monitored using an excitation wavelength of 485 nm and an emission wavelength of 528 nm at 37° C. (Ferguson et al., 2006). Results are shown at one hour, at which point all fluorescence and absorbance changes as a function of time were linear. All readings were normalized to vehicle control after subtraction of fluorescence in the absence of CCM. Data are shown as the mean±S.D. of at least three wells. All experiments were repeated at least twice and results are shown.

ATX Kinetics Assays

ATX kinetics assays were performed using eight different concentrations of substrate and two different concentrations of inhibitor (ChemBridge, San Diego, Calif.). The FS-3 substrate concentrations ranged from 20-0.3 µM on the plate.

The normalized fluorescence results were plotted as a function of time in order to determine initial rates. The initial rates were plotted against the substrate concentration and a rectangular hyperbolic curve was fitted to the data using the KaleidaGraph software (Synergy Software, Reading, Pa., Version 4.03). The $K_m$ and $V_{max}$ were calculated from the resulting plots. Mode of inhibition was determined from the inhibitor effect on $K_m$ and $V_{max}$ values. The dissociation constant ($K_i$) for inhibitor binding was calculated for each of the inhibitors. $K_i$ for uncompetitive inhibition was calculated using Equation 1 (Cheng and Prusoff, 1973). Equation 2 was used for competitive inhibition (Cheng and Prusoff, 1973). The average substrate $K_m$ values, 3.7+/−1.9 µM (n=22), were calculated using the individual $K_m$ values determined using rectangular hyperbolic curve fitting of plots of initial velocity versus substrate concentration from of all inhibition analyses for FS-3. For mixed mode inhibition $K_i = IC_{50}$ was assumed (Burlingham and Widlanski, 2003).

Pharmacophores 4a-d were able to achieve hit rates of 28.6%, 18.5%, 21.1% and 32.3%, respectively. Pharmacophores 5a-d were able to achieve hit rates of 0%, 25.8%, 0%, and 35.0%, respectively. Pharmacophores 4d and 5d have been able identify the largest percentages of active ATX inhibitors. Pharmacophore 4b was able to identify the highly potent compounds NSC 5014 and NSC 12859 and 5b was able to identify NSC 75779. NSC 341348, which has and $IC_{50}$ of 2.50 µM, was identified from two pharmacophores, 4a and 4c. NSC 77520, which has an $IC_{50}$ of 4.07 µM, was identified from pharmacophore 4d. The following tables show these results:

TABLE 3

Preliminary screen of 102 identified compounds from the virtual screen.

| NSC # | % Response |
|---|---|
| 45622 | 16 ± 3.1 |
| 65574 | 20 ± 3.7 |
| 75779 | 20 ± 5.7 |
| 338310 | 24 ± 2.9 |
| 12859 | 27 ± 2.8 |
| 45620 | 28 ± 3.7 |
| 58057 | 29 ± 3.6 |
| 58058 | 30 ± 4.9 |
| 7815 | 32 ± 5.5 |
| 43891 | 32 ± 9.1 |
| 77520 | 32 ± 2.7 |
| 80903 | 32 ± 2.6 |
| 65575 | 33 ± 3.7 |
| 79744 | 35 ± 2.9 |
| 65576 | 35 ± 5.8 |
| 79742 | 36 ± 2.5 |
| 79593 | 37 ± 2.6 |
| 5014 | 39 ± 4.3 |
| 65573 | 39 ± 3.8 |
| 79743 | 39 ± 2.7 |
| 47764 | 41 ± 4.3 |
| 11246 | 42 ± 6.0 |
| 65851 | 42 ± 3.5 |
| 65855 | 43 ± 3.8 |
| 341348 | 43 ± 2.8 |
| 65869 | 46 ± 6.7 |
| 47755 | 47 ± 3.7 |
| 65848 | 48 ± 4.8 |
| 7234 | 49 ± 6.1 |
| 11243 | 49 ± 6.1 |
| 75963 | 51 ± 4.4 |
| 47752 | 52 ± 5.4 |
| 65560 | 56 ± 4.9 |

TABLE 3-continued

Preliminary screen of 102 identified compounds from the virtual screen.

| NSC # | % Response |
|---|---|
| 12149 | 57 ± 6.5 |
| 8681 | 55 ± 5.5 |
| 8682 | 52 ± 7.7 |
| 34928 | 51 ± 6.5 |
| 106024 | 62 ± 2.5 |
| 79737 | 62 ± 2.8 |
| 47750 | 68 ± 5.8 |
| 47767 | 61 ± 3.7 |
| 51533 | 67 ± 4.0 |
| 65860 | 66 ± 4.4 |
| 1741 | 60 ± 4.6 |
| 44654 | 61 ± 4.3 |
| 45616 | 64 ± 3.0 |
| 80902 | 73 ± 4.5 |
| 65540 | 71 ± 4.4 |
| 65544 | 76 ± 5.1 |
| 65571 | 74 ± 5.5 |
| 65829 | 71 ± 4.0 |
| 65836 | 71 ± 4.6 |
| 34936 | 73 ± 9.0 |
| 37215 | 79 ± 3.7 |
| 47747 | 73 ± 3.0 |
| 7581 | 70 ± 4.8 |
| 11242 | 73 ± 3.7 |
| 11244 | 78 ± 7.0 |
| 12856 | 71 ± 5.4 |
| 16223 | 77 ± 9.8 |
| 71960 | 88 ± 5.3 |
| 79723 | 83 ± 3.2 |
| 47762 | 83 ± 5.5 |
| 58055 | 89 ± 3.9 |
| 34937 | 87 ± 3.1 |
| 45174 | 89 ± 3.2 |
| 1698 | 89 ± 5.1 |
| 8646 | 88 ± 9.2 |
| 34936 | 83 ± 5.8 |
| 12858 | 98 ± 7.4 |
| 32275 | 94 ± 6.5 |
| 2532 | 95 ± 5.7 |
| 4368 | 99 ± 2.8 |
| 5359 | 94 ± 2.6 |
| 7795 | 99 ± 5.0 |
| 7804 | 96 ± 6.4 |
| 2460 | 99 ± 3.1 |
| 36701 | 98 ± 3.7 |
| 37203 | 92 ± 9.1 |
| 39858 | 93 ± 4.6 |
| 46954 | 92 ± 3.9 |
| 47470 | 90 ± 3.2 |
| 47471 | 95 ± 3.0 |
| 48775 | 98 ± 5.5 |
| 48776 | 94 ± 3.5 |
| 55736 | 95 ± 3.9 |
| 373963 | 96 ± 2.5 |
| 332542 | 96 ± 3.7 |
| 306423 | 94 ± 3.6 |
| 270069 | 97 ± 2.4 |
| 212086 | 95 ± 4.3 |
| 205756 | 98 ± 3.1 |
| 5000 | 100 ± 5.5 |
| 7820 | 110 ± 5.7 |
| 12188 | 105 ± 8.0 |
| 12857 | 100 ± 7.3 |
| 13232 | 101 ± 9.0 |
| 15408 | 100 ± 7.9 |
| 37204 | 106 ± 60.5 |
| 47725 | 116 ± 4.2 |
| 47749 | 103 ± 58.1 |
| 56207 | 100 ± 4.2 |

TABLE 4

Calculated $IC_{50}$ data for the 30 active compounds.

| NSC # | $IC_{50}$ |
|---|---|
| 12859 | 805 nM |
| 75779 | 1.26 μM |
| 5014 | 1.27 μM |
| 341348 | 2.50 μM |
| 77520 | 4.07 μM |
| 80903 | 5.88 μM |
| 79593 | 6.36 μM |
| 7234 | 7.02 μM |
| 79742 | 7.04 μM |
| 338310 | 7.96 μM |
| 79743 | 8.33 μM |
| 45620 | 8.85 μM |
| 65851 | 9.50 μM |
| 11246 | 10.20 μM |
| 79744 | 11.52 μM |
| 45622 | 11.61 μM |
| 58057 | 11.63 μM |
| 65574 | 12.02 μM |
| 11243 | 12.57 μM |
| 7815 | 13.43 μM |
| 58058 | 13.84 μM |
| 43891 | 13.92 μM |
| 65848 | 15.19 μM |
| 65576 | 15.51 μM |
| 65855 | 17.44 μM |
| 47764 | 18.23 μM |
| 65575 | 18.56 μM |
| 65573 | 19.08 μM |
| 65869 | 22.67 μM |
| 47755 | 37.61 μM |

The determination of these inventive ATX inhibition compounds was thus based upon a modified pharmacophore model generation that provided a highly surprising 30% confidence rate in terms of ATX inhibition measurements. As such, the ability to predict proper autotaxin inhibition compounds is extremely difficult; however, through this modified pharmacophore modeling method, a relatively and unexpectedly high acceptance rate provides a surprisingly good confidence rate for the derived compounds generated in such a manner. In essence, this determination of suitable ATX inhibitors through a method that generated fewer than 300 initial compounds for testing from an initial database of 250,000 structures, and ultimately resulted in just over 100 compounds for final analysis of ATX inhibition was unexpectedly good and shows the potential value for such types of determinations through the avoidance of testing thousands of potential compounds through rough ATX inhibition screenings. The pharmacophore model, particularly in modified form to increase the restrictive result if an entire 6-point parent pharmacophore is followed, thus permits a method of providing suitable results for ATX inhibiting compounds, not to mention potentially any other type of pharmaceutical compound, without the need to invest unreasonable time and resources to such an end. Ultimately, the inventive method supplied a group of potentially effective ATX inhibitors as presented:

TABLE 5
Highly potent ATX inhibitors identified through the pharmacophore screen.
| Compound Number and Structure | % ATX Acitivity (10 μM) | IC$_{50}$ (μM) |
|---|---|---|
| 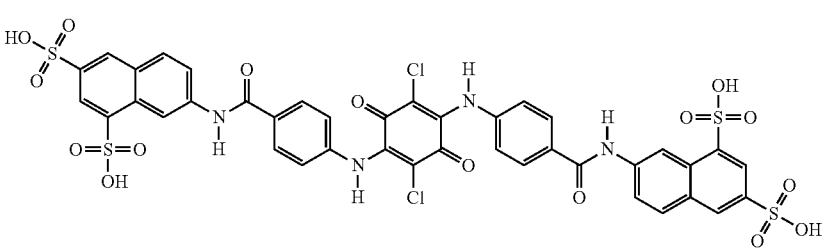<br>NSC 12859 | 27 ± 2.8 | 0.805 |
| 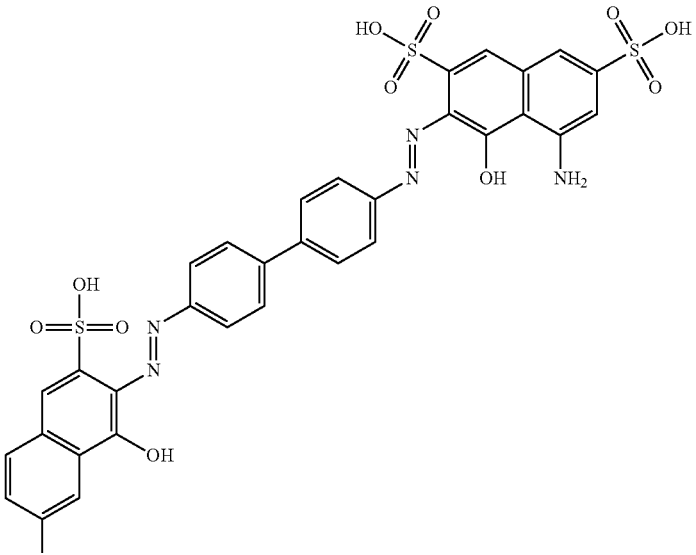<br>NSC 75779 | 20 ± 5.7 | 1.26 |
| 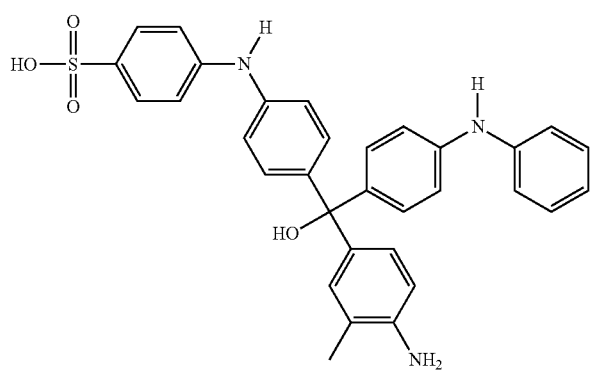<br>NSC 5014 | 39 ± 4.3 | 1.27 |

TABLE 5-continued
Highly potent ATX inhibitors identified through the pharmacophore screen.
| Compound Number and Structure | % ATX Acitivity (10 μM) | IC$_{50}$ (μM) |
|---|---|---|
| 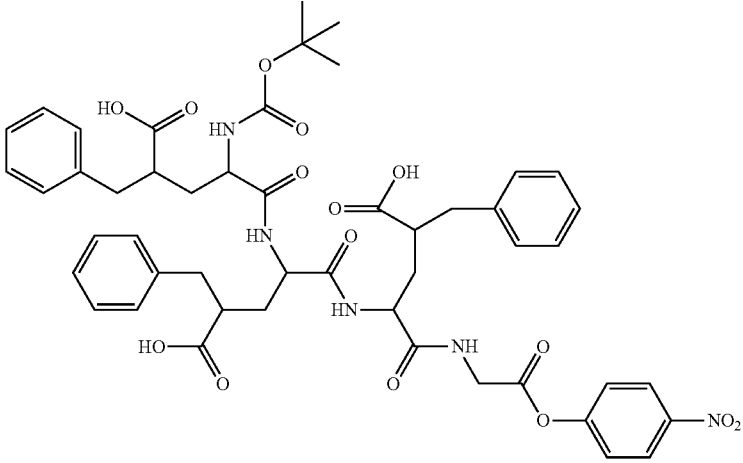<br>NSC 341348 | 43 ± 2.8 | 2.50 |
| 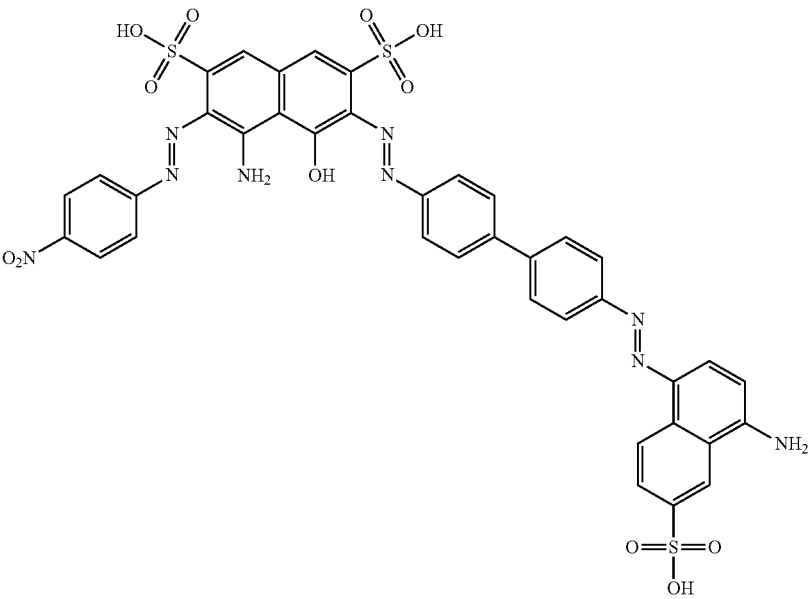 [SMILES: Nc1ccc(/N=N/c2ccc(-c3ccc(/N=N/c4c(S(=O)(=O)O)cc5cc(S(=O)(=O)O)c(/N=N/c6ccc([N+](=O)[O-])cc6)c(N)c5c4O)cc3)cc2)c2ccc(S(=O)(=O)O)cc12] | 32 ± 2.7 | 4.07 |

TABLE 5-continued

Highly potent ATX inhibitors identified through the pharmacophore screen.

Compound Number and Structure    % ATX Acitivity (10 μM)    IC$_{50}$ (μM)

NSC 75520

These compounds noted above exhibit a reduction in ATX-catalyzed FS-3 hydrolysis of target tumor cells by 54% or more at a concentration of about 10 μM. Such a reduction in activity of autotaxin is basically in terms of potential conversion of LPC to LPA, particularly through structural modifications to prevent placement of the LPC compound into the active site of the modified autotaxin enzyme. These naphthalene sulfones (first two above), phenylsulfones (next two), and peptides with unnatural amino acids (last two), thus exhibit excellent ATX inhibition properties, which thus correlate, with the Lipinski's rules criteria, to potentially effective orally ingestable treatments for various patient types, particularly for certain cancer patients.

The term "napthalene sulfone" is intended to encompass any compound including a naphthalene and a sulfone group and that comports with the six-point pharmacophore criteria measurements set forth above. Likewise, the term "phenylsulfone" is intended to encompass any compound including a phenylsulfone group comporting with the pharmacophore structure in such a manner. As well, the term "peptide with unnatural amino acids" is intended to encompass any compound including a peptide group and simultaneously amino acids formed through synthetic routes therein and that comports in structure to the pharmacophore as stated above.

Coupled, again, with the oral bioavailability characteristics noted above, these compounds hold great promise in providing orally ingestable tumor treatments for certain cancers.

As alluded to above, as well, it is believed that the differing compounds exhibiting similar base point structures through the pharmacophore comparisons herein, may also exhibit effective synergistic qualities in providing differing levels and/or degrees of ATX inhibition when utilized as prescribed above. As such, the potential for further improvements in ATX inhibition methods may be available through the utilization of such combinations of compounds.

There are, of course, many alternative embodiments and modifications of the present invention which are intended to be included within the spirit and scope of this invention.

What we claim is:

1. A method for treating a patient to reduce autotaxin activity within the subject patient's body, said method involving the introduction within the subject patient of at least one compound selected from the group consisting of at least one naphthalene sulfone, at least one phenylsulfone, and any mixtures thereof.

2. The method of claim 1 wherein said at least one compound is at least one naphthalene sulfone.

3. The method of claim 2 wherein said at least one naphthalene sulfone meets the structure of at least one of Compounds A and B:

A)

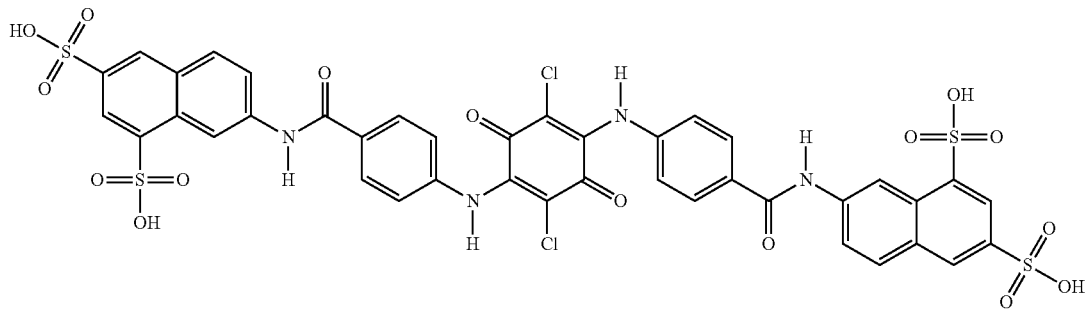

B)

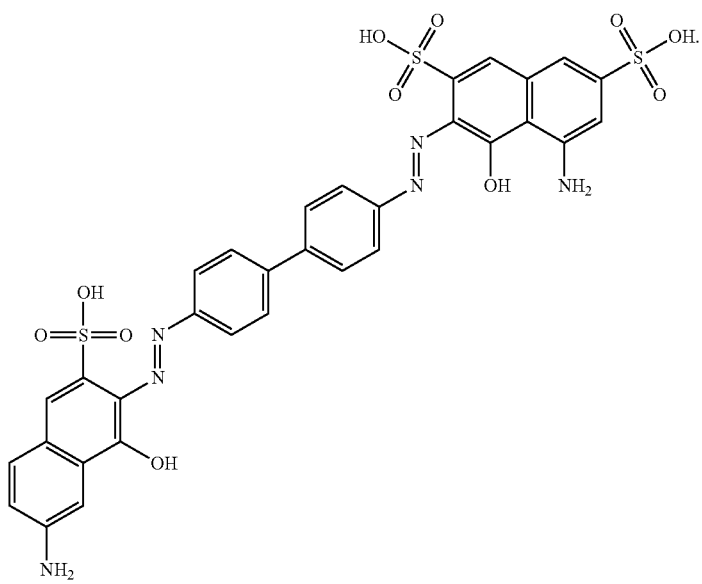

4. The method of claim 1 wherein said at least one compound is at least one phenylsulfone.

5. The method of claim 4 wherein said at least one phenylsulfone meets the structure of at least one of Compounds C and D:

C)

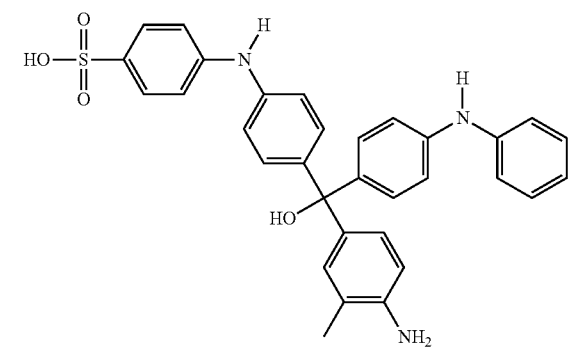

D)

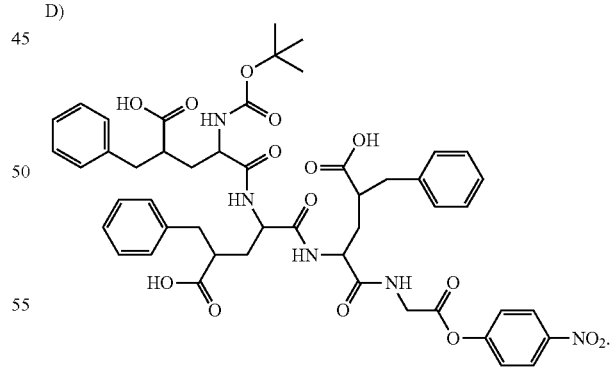

6. A method of inhibiting autotaxin from converting lysophosphatidyl choline to lysophophatidic acid comprising the step of reacting autotaxin with at least one compound selected from the group consisting of at least one naphthalene sulfone, at least one phenylsulfone, and any mixtures thereof.

7. The method of claim 6 wherein said at least one compound is at least one naphthalene sulfone.

8. The method of claim 7 wherein said at least one naphthalene sulfone meets the structure of at least one of Compounds A and B:

A)

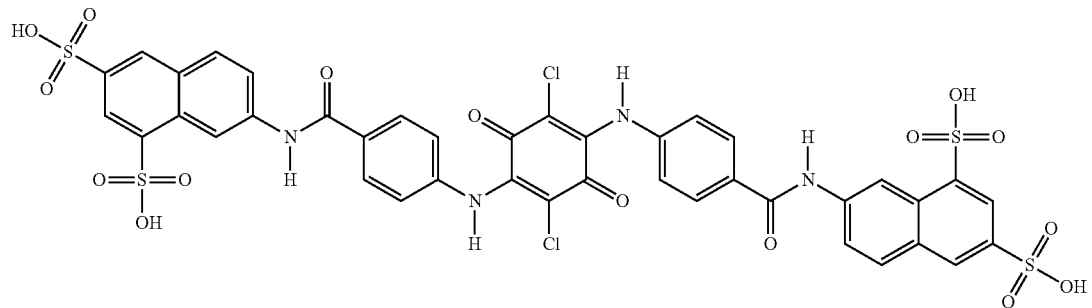

B)

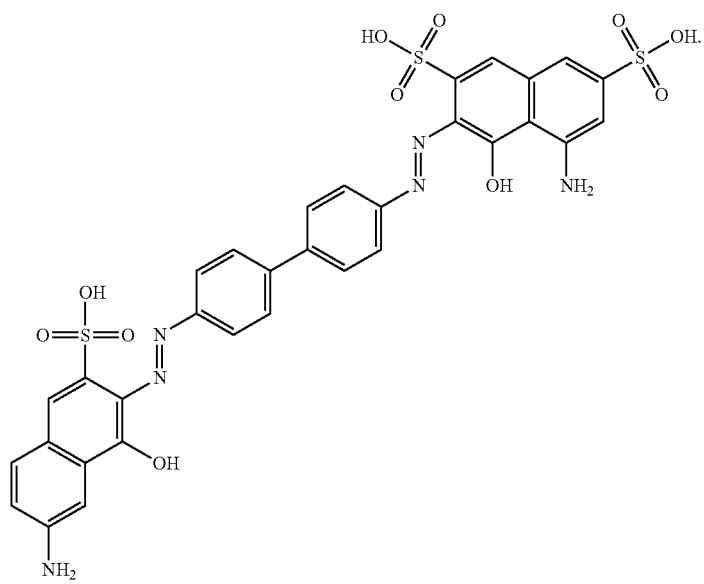

9. The method of claim 6 wherein said at least one compound is at least one phenylsulfone.

10. The method of claim 9 wherein said at least one phenylsulfone meets the structure of at least one of Compounds C and D:

C)

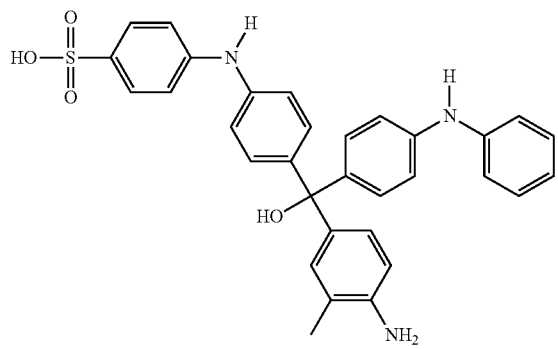

-continued

D)

11. An orally digestable composition including at least one autotaxin inhibitor compound selected from the group consisting of at least one compound selected from the group consisting of at least one naphthalene sulfone, at least one phenylsulfone, and any mixtures thereof, wherein said at least one phenylsulfone meets the structure of at least one of C and D:

C)
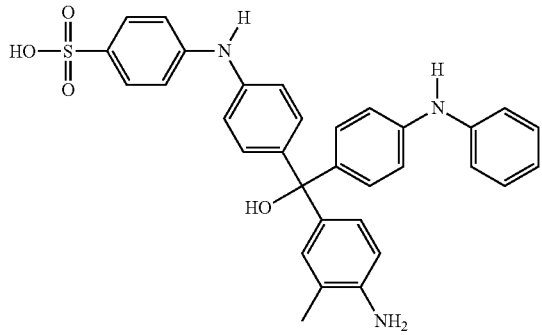
D)
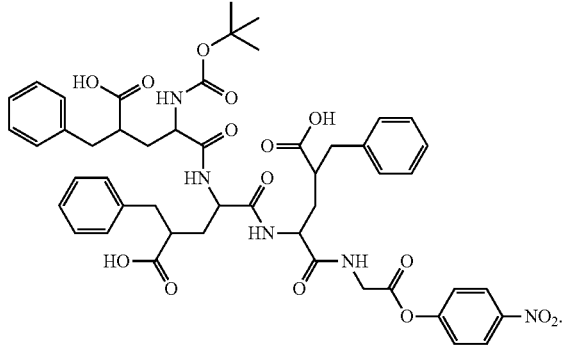
12. The method of claim 11 wherein said at least one compound is at least one naphthalene sulfone.
13. The composition of claim 12 wherein said at least one naphthalene sulfone meets the structure of at least one of Compounds A and B:
A)
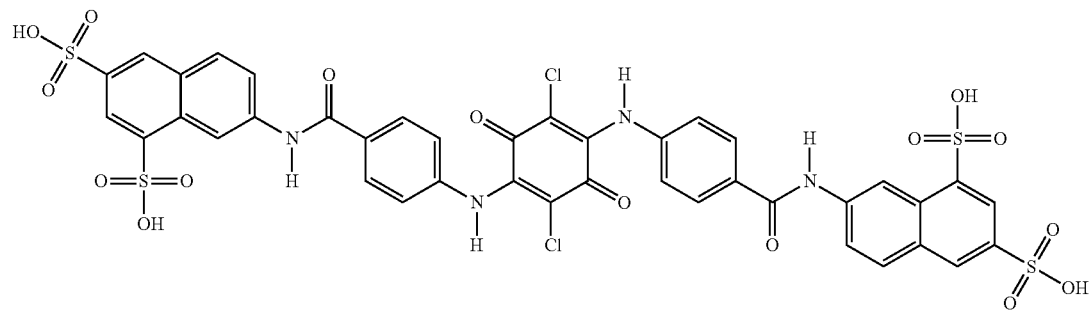
B)
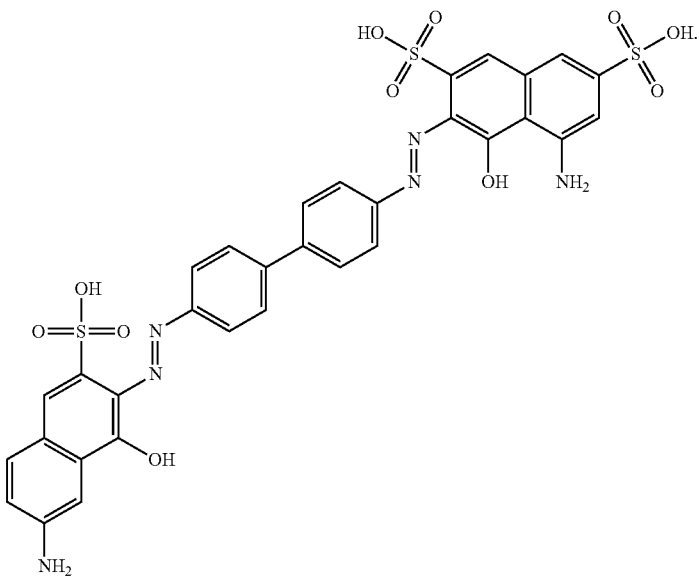
14. The method of claim 11 wherein said at least one compound is at least one said phenylsulfone compounds defined therein.
* * * * *